US011078152B2

(12) United States Patent
Coquerel et al.

(10) Patent No.: US 11,078,152 B2
(45) Date of Patent: Aug. 3, 2021

(54) METHOD FOR RESOLUTION OF BACLOFEN SALTS

(71) Applicant: Universite de Rouen, Mont-Saint-Aignan (FR)

(72) Inventors: Gérard Coquerel, Mont-Saint-Aignan (FR); Julien Mahieux, Ecoteaux (CH); François-Xavier Gendron, Autretot (FR)

(73) Assignee: Universite de Rouen, Mont-Saint-Aignan (FR)

( * ) Notice: Subject to any disclaimer, the term of this patent is extended or adjusted under 35 U.S.C. 154(b) by 223 days.

(21) Appl. No.: 16/318,565

(22) PCT Filed: Jul. 20, 2017

(86) PCT No.: PCT/FR2017/051992
§ 371 (c)(1),
(2) Date: Jul. 2, 2019

(87) PCT Pub. No.: WO2018/015677
PCT Pub. Date: Jan. 25, 2018

(65) Prior Publication Data
US 2019/0345098 A1    Nov. 14, 2019

(30) Foreign Application Priority Data
Jul. 22, 2016   (FR) ...................................... 1657054

(51) Int. Cl.
*C07C 229/34*    (2006.01)
*C07C 227/34*    (2006.01)

(52) U.S. Cl.
CPC .......... *C07C 227/34* (2013.01); *C07C 229/34* (2013.01)

(58) Field of Classification Search
CPC ............................ C07C 229/34; C07C 227/34
USPC ........................................... 562/443; 514/561
See application file for complete search history.

(56) References Cited

U.S. PATENT DOCUMENTS 6,022,409 A    2/2000   Coquerel et al.

FOREIGN PATENT DOCUMENTS

| WO | 97/22579 A1 | 6/1997 |
| WO | 2011/073300 A1 | 6/2011 |

OTHER PUBLICATIONS

International Search Report issued in corresponding International Patent Application No. PCT/FR2017/051992 dated Oct. 23, 2017.
Mazzenga et al., "The transdermal delivery of zwitterionic drugs I: the solubility of zwitterion salts," Journal of Controlled Release, 16: 77-88 (1991).

*Primary Examiner* — Joseph R Kosack
*Assistant Examiner* — Sagar Patel
(74) *Attorney, Agent, or Firm* — Morgan, Lewis & Bockius LLP

(57) ABSTRACT

The invention relates to the field of resolution of chiral compounds existing in the form of two optical antipodes (enantiomers), such as Baclofen. More particularly, the invention relates to the production of the pure enantiomer (R)(−) Baclofen, of chemical nomenclature (R)-4-amino-3-(4-chlorophenyl)-butanoic acid, and the hydrogen maleate salt thereof. More specifically, the invention relates to the resolution of hydrogen maleate salts of racemic Baclofen by preferential crystallisation and particularly by the AS3PC method (auto-seeded and programmed polythermal preferential crystallisation).

14 Claims, 9 Drawing Sheets

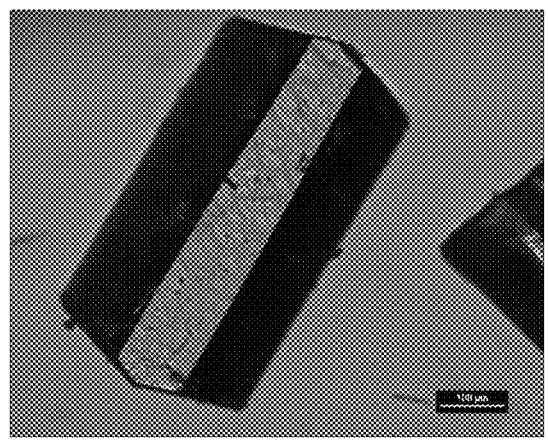
Figure 1
Figure 2
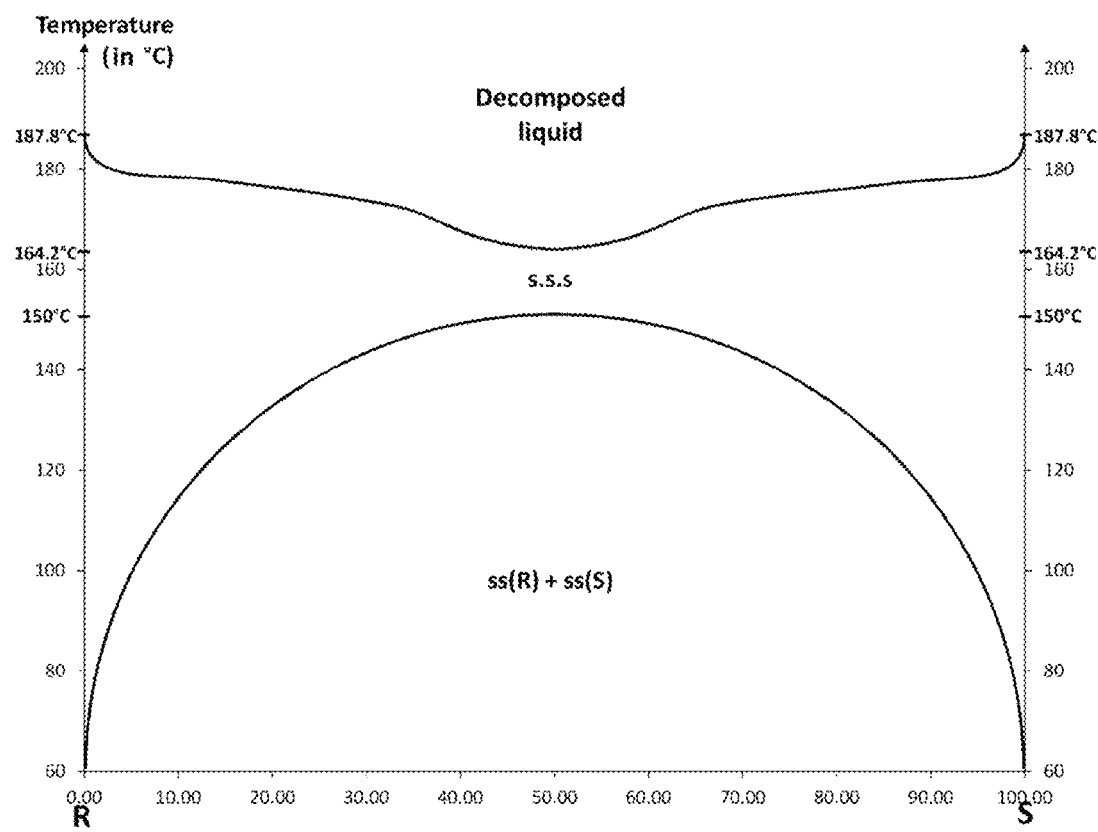
sss: total substitution solid solution
ss(S): partial solid solution enriched in Bahma (S) enantiomer
ss(R): partial solid solution enriched in Bahma (R) enantiomer Liq: liquid
<S>: (S) enantiomer in solid form
<R>: (R) enantiomer in solid form Liq: liquid
<S>: (S) enantiomer in solid form
<R>: (R) enantiomer in solid form
<RS>: racemic compound in solid form r.s.s.: saturated solution of racemic Bahma salt
sat. sol.: saturated solution enriched in Bahma (S) or (R) enantiomer
U.S.S: under-saturated solution
ssR: partial solid solution enriched in Bahma (R) enantiomer
ssS: partial solid solution enriched in Bahma (S) enantiomer
— · — · — · : isopleth section
$L_0$ = saturated racemic solution
$P_0L_0$ and $P_1L_1$: conodes

METHOD FOR RESOLUTION OF BACLOFEN SALTS

TECHNICAL FIELD

The present invention relates to the field of resolving chiral compounds existing in the form of two optical antipodes (enantiomers), such as baclofen.

More particularly, the invention relates to the preparation of the pure (R)(−)-baclofen and S(+)-baclofen enantiomers, the chemical name of which is (R)-4-amino-3-(4-chlorophenyl)butanoic acid and (S)-4-amino-3-(4-chlorophenyl)butanoic acid and the hydrogen maleate salt thereof.

Most especially, the present invention relates to the resolution of the hydrogen maleate salts of racemic baclofen by preferential crystallization and especially via the AS3PC (auto-seeded programmed polythermic preferential crystallization) process or the ASPreCISE (auto-seeded preferential crystallization induced by solvent evaporation) process.

BACKGROUND OF THE INVENTION

Racemic baclofen is represented by the general formula (I) below:

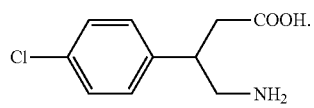

(I)

The pure (R)(−)-baclofen enantiomer is represented by the general formula (II) below:

(II)

The pure (S)(−)-baclofen enantiomer is represented by the general formula (III) below:

(III)

Baclofen, also known under the name Lioresal, is a medicament used as a muscle relaxant for treating the painful cramps accompanying multiple sclerosis and certain paralyses.

In France, the Agence Nationale de Sécurité du Medicament et des Produits de Santé (ANSM) [National Agency for the Safety of Drugs and Health Products] recently granted a temporary recommendation for use of baclofen for the treatment of alcohol dependency.

In its current therapeutic use, this molecule is administered in the form of a racemic mixture. Since the R(−) enantiomer is three times more active than the S(+) enantiomer, it appears advantageous, especially for long treatments, to prescribe only the more active R(−) absolute configuration. As such, there will be fewer side products in the body and the dosage can be reduced while maintaining the benefit of the activity.

To produce the R(−) form, the methods described in the literature involve either an asymmetric synthesis starting with a racemic mixture or a prochiral compound with catalysts, or an enantioselective synthesis starting with a chiral reagent.

For example, it is possible to use enzymatic catalysts, such as bacteria of the *Rhodococcus* sp. type, as described in M. X. Wang, S. M. Zhao, Tetrahedron Lett. 2002, 43, 6617-6620, to access R(−)-baclofen according to the following scheme:

The article *Canadian Journal of Chemistry*, 1994, 72(11), 2312-2317 also discloses a route for the asymmetric synthesis of R(−)-baclofen involving desymmetrization of a prochiral glutarate with chymotrypsin according to the following scheme:

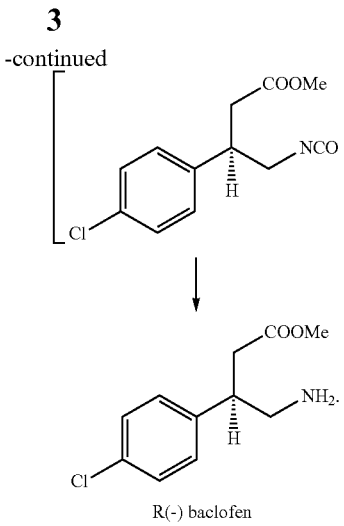

Finally, patent application WO 94/02443 describes an enantioselective synthesis of R(−)-baclofen starting with an S-pyroglutamic acid derivative according to the following scheme:

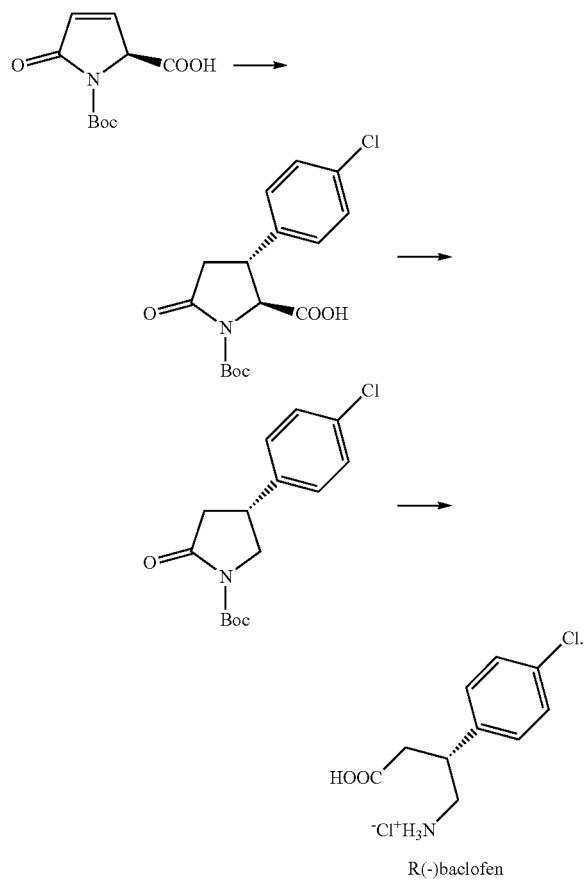

However, these methods involve reagents that are expensive and difficult to implement industrially. Furthermore, the final yield of R(−)-baclofen is relatively low. In addition, due to the number of synthetic steps, the final product is contaminated with impurities that must be removed via purification steps so as to obtain a product that is pure enough to be administered as a medicament.

In this context, the inventors developed a process for separating the baclofen enantiomers starting with a racemic mixture. This process is advantageously industrially implementable and does not require the use of chiral derivatives. Furthermore, the steps of the process of the present invention are easy to perform and there is no loss of starting material by virtue of the successive recyclings.

This aim is achieved by means of the application of the process of preferential crystallization to racemic baclofen in salt form. Thus, the invention relates most particularly to the application, to a racemic baclofen hydrogen maleate salt, of resolution via preferential crystallization of each of its enantiomers, making it possible to obtain the R(−)-baclofen eutomer in an enantiomerically and chemically pure form.

The racemic baclofen hydrogen maleate salt may be resolved via any type of preferential crystallization, especially the most advantageous, i.e. auto-seeded processes.

In particular, the AS3PC preferential crystallization process has been the subject of an entirely novel development excluding the constraining use of crystallization seeds (i.e. without seeding). This process is described, for example, in the following patents and patent applications: FR 2 710 337, WO 95/08522, EP 0 720 595 and U.S. Pat. No. 6,022,409 and in G. Coquerel, *Preferential Crystallization* in *Topics in Current Chemistry, Novel Optical Resolution Technologies*, Springer, Berlin, Heidelberg, Eds. K. Sakai, N. Hirayama and R. Tamura, 2007, 269, 1-51. This process is named AS3PC, meaning Auto-Seeded Programmed Polythermic Preferential Crystallization Another auto-seeded preferential crystallization process is described in patent application WO 2011/07330. This process is known by the abbreviation ASPreCISE meaning Auto-Seeded PREferential Crystallization Induced by Solvent Evaporation.

Preferential crystallization processes are based on the alternating stereoselective crystallization of the two (R) and (S) enantiomers, of the same racemic chemical species crystallizing in conglomerate form, in a medium which may be a solvent or a mixture of solvents or a set of constituents including the solvent(s), and for a given temperature range ΔT. Within this temperature range, this racemic mixture, which is in thermodynamic equilibrium with its saturated solution, is constituted of two types of crystals each containing only molecules of the same absolute configuration.

Knowledge of these (R)-enantiomer—(S)-enantiomer—solvent heterogeneous equilibria provides data that are exploited for performing efficient resolution by preferential crystallization.

The studies conducted by the Applicant show that racemic baclofen does not crystallize in the form of a conglomerate. This means that neither the preferential crystallization process AS3PC or ASPreCISE nor any other preferential crystallization process can be applied.

In the perspective of implementing such a process, the search for a baclofen salt allowing chiral discrimination was performed by addition of a coformer, such as an acid, a base or an alkali metal. The full list of the various coformers tested is presented in Table 1 below:

TABLE 1

Coformers: acids, bases or alkali metals
(the compounds in bold are those for which a new phase is observed, the new
phase being a co-crystal comprising baclofen and the coformer)

| | | |
|---|---|---|
| 4-nitrobenzoic acid | cholic acid | adipic acid |
| 3,4-dichlorobenzoic acid | 3-bromo-4-nitrobenzoic acid | 4-hydroxybenzenesulfonic acid |
| 4-fluoro-3-nitrobenzoic acid | 3-fluoro-4-nitrobenzoic acid | dichloroacetic acid |
| 2-chloro-4-nitrobenzoic acid | 2,5-dinitrobenzoic acid | tetrafluoroboric acid |
| 2,4-dihydroxybenzoic acid | 3-methoxy-4-nitrobenzoic acid | trifluoromethanesulfonic acid |
| 4-hydroxybenzoic acid | 2-chloro-3,5-dinitrobenzoic acid | acetic acid |
| 4-chloro-3,5-dinitrobenzoic acid | 2-methyl-3,5-dinitrobenzoic acid | 2,4-diaminobenzenesulfonic acid |
| 3,5-dinitro-4-toluic acid | 3,5-dinitrosalicylic acid | methanesulfonic acid |
| 4-methyl-3-nitrobenzoic acid | 3-bromo-5-nitrobenzoic acid | 4-nitrobenzenesulfonic acid |
| 3-nitro-5-(trifluoromethyl)benzoic acid | salicylic acid | trichloroacetic acid |
| 3,4-dinitrobenzoic acid | hydrocinnamic acid | benzenesulfonic acid |
| citraconic acid | 5-chloro-2-nitrobenzoic acid | 3,5-diamino-2,4,6-trimethylbenzenesulfonic acid |
| 3,5-dinitrobenzoic acid | 2,5-dichlorobenzoic acid | 1,2-phenylenediacetic acid |
| o-toluic acid | fumaric acid | 2,5-diaminobenzenesulfonic acid |
| 3-nitrobenzoic acid | 2-phenylbutyric acid | bromoacetic acid |
| 4-chloro-3-nitrobenzoic acid | 2-tetrahydrofolic acid | ethanesulfonic acid |
| 3-methyl-4-nitrobenzoic acid | trans-3,4-dimethoxy cinnamic acid | methanesulfonic acid |
| oxalic acid | 3-phenylbutyric acid | methoxyacetic acid |
| methylsulfamic acid | 4-chlorobenzenesulfonic acid | hexamethylenetetramine |
| stearic acid | butylethylhydroxypropionic acid | diphenylamine |
| undecanedioic acid | trans-cinnamic acid | tetrahydrofurfurylamine |
| cis,cis-muconic acid | glutaric acid | tert-butylamine |
| 2,4-diaminobenzenesulfonic acid | isophthalic acid | benzylamine |
| glycolic acid | itaconic acid | n-butylamine |
| pimelic acid | malonic acid | ethylene diamine |
| tetradecanedioic acid | n-butyric acid | N,N'-dibenzylethylenediamine |
| mucic acid | p-tolylacetic acid | ethanolamine |
| suberic acid | propionic acid | ammonia |
| sebacic acid | 1H-benzimidazole-2-sulfonic acid | triethanolamine |
| dodecanedioic acid | 1-naphthalenesulfonic acid | potassium hydroxide |
| uric acid | 3-pyridinesulfonic acid | calcium hydroxide |
| succinic acid | chloroacetic acid | magnesium hydroxide |
| boric acid | 1-hydroxy-2-naphthoic acid | aluminum hydroxide |
| p-toluenesulonic acid monohydrate | 1-propanesulfonic acid | strontium hydroxide |
| citric acid | iodoacetic acid | lithium hydroxide monohydrate |
| nitric acid | hydrochloric acid | sodium hydroxide |
| sulfuric acid | bromic acid | rubidium formate hydrate |
| phosphoric acid | hydriodic acid | trifluoroacetic acid |
| sulfamic acid | perchloric acid | pyrophosphoric acid |

However, entirely unexpectedly, the Applicant has found that baclofen forms with maleic acid a salt which crystallizes without formation of a solvate in the majority of the usual solvents and without formation of a eutectic mixture in molten medium. This saline derivative also has the advantage of being a pharmaceutically acceptable and inexpensive salt. Surprisingly, this salt shows virtually total chiral discrimination at room temperature but no chiral discrimination at high temperature. This property was used to resolve the racemic mixture with an optimum yield by repeated application of preferential crystallization. Furthermore, the resolution process may be performed in water using AS3PC auto-seeded resolution for greater ease of exploitation at the industrial scale.

DESCRIPTION OF THE INVENTION

One subject of the present invention is a racemic baclofen hydrogen maleate (Bahma) salt with a melting/decomposition point of 164±1° C.

Another subject of the invention is the use of the racemic baclofen hydrogen maleate salt for resolving the (S) and (R) enantiomers of baclofen.

A subject of the present invention is also a process for resolving the (S) and (R) enantiomers of baclofen, in which racemic baclofen is transformed into the racemic baclofen hydrogen maleate salt in the presence of maleic acid and in which said salt is resolved by preferential crystallization to separate the two (S) and (R) enantiomers.

A subject of the present invention is also a process for the enantiomeric purification of baclofen hydrogen maleate salts, comprising the recrystallization of baclofen hydrogen maleate salts in a solvent.

A subject of the present invention is also a baclofen hydrogen maleate salt of R(−) absolute configuration or a baclofen hydrogen maleate salt as obtained via the processes of the present invention, for its use in the treatment of multiple sclerosis, paralyses or alcohol dependency.

DETAILED DESCRIPTION

The racemic baclofen hydrogen maleate salt that is the subject of the present invention has a melting/decomposition point of 164±1° C. The melting/decomposition point is measured by differential scanning calorimetry (DSC) according to the method described below. The term "Bahma" used in the present patent application denotes "baclofen hydrogen maleate".

The melting/decomposition point corresponds to the melting point of the Bahma salt which is followed or accompanied by decomposition of the Bahma salt. Specifically, the Bahma salt may undergo one or more decomposition reactions, for example the formation of maleic anhydride or the esterification of baclofen or another decomposition reaction.

Said salt corresponds to the formula $[C_{10}H_{13}ClNO_2]^+$, $[C_4H_3O_4]^-$. Thus, the amine function of baclofen is protonated and there is only one baclofen molecule and only one hydrogen maleate molecule in the asymmetric unit. The molar mass of the salt is 329.73 g.mol$^{-1}$.

Said salt may especially be obtained by dissolving a racemic mixture of baclofen and of maleic acid in stoichiometric proportions in a solvent or a mixture of solvents.

The salification reaction may especially be performed in a solvent chosen from acetone, water, methanol, a water/n-propanol azeotrope and mixtures thereof.

In order to ensure good crystallization, it is advantageous to dissolve the baclofen and the maleic acid in the smallest possible volume of solvent. Furthermore, to achieve a homogeneous solution, the mixture may be heated.

After dissolution of the solids, the solution is allowed to return to room temperature and the crystals form by evaporation of the solvent within a few days.

The single crystals obtained have a characteristic facies with zones of total reflection, along the axis of longest development of the crystal, as shown in FIG. 1.

The (R) and (S) salts of baclofen hydrogen maleate of the present invention exhibit a total solid solution at high temperature, especially at a temperature above 150° C. Specifically, the phase diagram of the two enantiomers of FIG. 2 shows that there is a single one-phase domain, i.e. a total solid solution, above 150° C. Below this temperature, which corresponds exactly to the maximum critical demixing point in the solid state of the racemic mixture, there is chiral discrimination in the solid state, which becomes increasingly amplified as the temperature is lowered.

Unexpectedly, FIG. 2 also shows that there is virtually total chiral discrimination at a temperature of less than or equal to 70° C. Thus, below 70° C., the one-phase domain is very low in composition, i.e. less than <1% of the other enantiomer, on each side of the binary phase diagram. This large demixing gap offers very substantial chiral discrimination in the solid state which may be exploited to perform resolution by preferential crystallization or preparative enantiomeric purification, i.e. without loss of enantiomeric excess.

This behavior was all the less anticipated since baclofen and maleic acid offer multiple possibilities for directed hydrogen bonds that are sparingly favorable to the formation of a solid solution. This very rare case of total solid solution with demixing in the solid state differs from the more conventional cases of conglomerates with partial solid solution, the phase diagram of which is represented in FIG. 3.

It should be noted that many baclofen salts other than Bahma were studied (cf. Table 1 above). However, their binary phase diagrams, similar to that shown in FIG. 4, do not present a total solid solution or chiral discrimination, which does not make it possible to envisage resolution by preferential crystallization.

Thus, owing to its specific behavior, baclofen hydrogen maleate is, in principle, entirely suitable for use in resolving the (S) and (R) enantiomers of baclofen.

A subject of the invention is also a process for resolving the (S) and (R) enantiomers of baclofen, in which racemic baclofen is transformed into racemic baclofen hydrogen maleate salt in the presence of maleic acid. The racemic Bahma salt obtained is then resolved by preferential crystallization to separate the two (S) and (R) enantiomers.

Resolution of the racemic Bahma salt may especially be performed by auto-seeded preferential crystallization (AS3PC or ASPreCISE) or by seeded preferential crystallization, preferably by auto-seeded preferential crystallization.

According to a particular embodiment of the process of the present invention, the preferential crystallization is performed with a solvent chosen from an alcoholic solvent, an aqueous solution, an acidic aqueous solution and mixtures thereof.

Examples of alcoholic solvents that may be used are methanol, ethanol, n-propanol and mixtures thereof, in particular n-propanol.

According to a particular embodiment, the solvent is an azeotropic mixture of n-propanol and water.

According to a preferred embodiment, the preferential crystallization is performed with an acidic aqueous solution, the acid being chosen from hydrochloric acid, acetic acid, nitric acid, preferably an aqueous hydrochloric acid solution, more preferentially an aqueous 2 mol/L hydrochloric acid solution.

Indeed, the solubility of Bahma in an acidified aqueous solution is greater than that of Bahma in water or in an azeotropic mixture of n-propanol and water. This better solubility makes it possible to increase the productivity of the preferential crystallization.

According to a particular embodiment, the preferential crystallization is auto-seeded and comprises the following steps:

a) a volume V of a saturated solution of racemic Bahma salt in a solvent is prepared at a temperature $T_L$;

b) at least 5% by weight of the first Bahma enantiomer to be recovered relative to the weight of the racemic Bahma salt is added;

c) the mixture is heated to a temperature $T_B = T_L + \Delta T$;

d) a cooling programming law is applied to the mixture from $T_B$ to $T_F$, $T_F$ being below $T_B$, such that the mixture maintains a low supersaturation which favors the growth of the first Bahma enantiomer present in the form of crystals, while prohibiting the spontaneous nucleation of the second Bahma enantiomer dissolved in the solution;

e) the crystals of the first Bahma enantiomer are harvested at the temperature $T_F$;

f) substantially the same mass of racemic Bahma salt as the mass of the harvest made in the preceding step is added to the mixture, the difference is made up with solvent to reach the volume V and the new combined mixture is brought to the temperature $T_B$;

g) the temperature $T_B$ is maintained for a time t so as to allow the system to return to thermodynamic equilibrium;

h) the same cooling programming law as in step (d) is applied to the mixture prepared in step (g) containing the second Bahma enantiomer, so that the mixture maintains a low supersaturation during the crystallization so as to promote the growth of the second Bahma enantiomer present in the form of crystals while at the same time prohibiting the spontaneous nucleation of the first Bahma enantiomer present in the solution;

i) the crystals of the second Bahma enantiomer are harvested at the temperature $T_F$;

j) substantially the same mass of racemic Bahma salt as the mass of the harvest made in the preceding step is added to the mixture, the difference is made up with solvent to reach the volume V and the new combined mixture is brought to the temperature $T_B$;

k) the temperature $T_B$ is maintained for a time t so as to allow the system to return to thermodynamic equilibrium;

l) steps (d) to (k) are repeated to successively obtain one and then the other of the two enantiomers.

In the above process, the solvent is as described previously, especially an azeotropic mixture of n-propanol and water or an acidic aqueous solution. The volume V of solvent used to obtain a saturated solution is determined as a function of the amount of racemic Bahma salt to be resolved and of the solubility of the racemic Bahma salt in the chosen solvent.

In step (b) of the above process, the amount of the first Bahma enantiomer added is at least 5% by weight relative to the weight of the racemic Bahma salt dissolved in the solvent, in particular from 5% to 15% by weight, more particularly from 5% to 10% by weight.

In step (c) of the above process, the temperature $T_L$ corresponds to the temperature of dissolution of the racemic mixture alone in the solvent according to step (a). According to a particular embodiment, the temperature $T_L$ ranges from 30 to 70° C.; preferably, $T_L$ ranges from 40 to 60° C. and more preferentially $T_L$ is 50° C.

In step (c) of the above process, the temperature $T_B$ corresponds to a temperature slightly above the dissolution temperature of the racemic mixture $T_L$. Thus, the temperature $T_B=T_L+\Delta T$ in which $\Delta T$ ranges from 1° C. to 10° C., in particular from 2° C. to 7° C., more particularly from 3° C. to 5° C.

Advantageously, in steps (d) and (h) of the above process, a stirring speed that increases slightly as a function of time is adapted throughout the duration of the crystal growth so that it is slow enough to favor growth of the first or the second Bahma enantiomer, while avoiding the generation of uncontrolled nucleation and attrition of crystals.

In the above process, the temperature $T_F$ depends on the amount of racemic Bahma salt that it is desired to resolve. According to a particular embodiment, the temperature $T_F$ ranges from 20 to 40° C.; preferably, $T_F$ ranges from 25 to 35° C.; more preferentially, $T_F$ is 30° C.

In the above process, the time t depends on the amount of racemic Bahma salt that it is desired to resolve. According to a particular embodiment, the time t is greater than 20 min, preferably from 25 min to 45 min, and more preferentially t is 30 min.

In steps (e) and (i) of the above process, the crystals of the first Bahma enantiomer and the crystals of the second Bahma enantiomer are harvested by filtration or centrifugation.

The crystals of the first Bahma enantiomer and the crystals of the second Bahma enantiomer obtained via the process that is the subject of the present invention may especially have an enantiomeric excess of greater than 80%. Said crystals may be recrystallized to obtain an enantiomeric excess of close to 100%, especially according to the enantiomeric purification process according to the invention described below. A suitable solvent for the recrystallization is a solvent chosen from acetone, water, methanol, the water/n-propanol azeotrope and mixtures thereof.

According to a second embodiment, the preferential crystallization is seeded and comprises the following steps:

a) a first homogeneous solution is prepared, composed of the racemic Bahma salt, of an excess of the first Bahma enantiomer to be recovered and of a solvent, the figurative point I of which, defined by the concentration and temperature variables $T_I$ ($T_I>T_{HOMO}$), is within the one-phase domain composed of the under-saturated solution;

b) a cooling programming law is applied to the one-phase mixture;

c) when the mixture reaches a temperature below the temperature $T_{HOMO}$, the solution is seeded with enantiomerically pure seeds of the first Bahma enantiomer to be recovered;

d) a stirring speed that increases slightly as a function of time is adapted throughout the crystal growth so that it is slow enough to favor growth of the first Bahma enantiomer;

e) the crystals of the first Bahma enantiomer are harvested;

f) the same mass of racemic Bahma salt as the mass of the harvest made in the preceding step is added to the mixture, and the new combined mixture is brought to the temperature $T_I$ ($T_I>T_{HOMO}$), the point I' being within the one-phase domain;

g) the same cooling programming law as in step (b) is applied to the one-phase mixture prepared in step (f) containing the second enantiomer, so that the mixture maintains a low supersaturation during the crystallization so as to promote growth of the second Bahma enantiomer during seeding;

h) when the mixture reaches a temperature below the temperature $T_{HOMO}$, the solution is seeded with enantiomerically pure seeds of the second Bahma enantiomer;

i) a stirring speed that increases slightly as a function of time is adapted throughout the crystal growth of the preceding step, so that it is slow enough to favor growth of this second Bahma enantiomer;

j) the crystals of the second Bahma enantiomer are harvested;

k) the same mass of racemic Bahma salt as the mass of the harvest made in the preceding step is added to the mixture, to obtain a solution whose composition is identical to that of the initial solution;

l) steps (b) to (k) are repeated to successively obtain one and then the other of the two enantiomers.

A subject of the present invention is also a process for the enantiomeric purification of Bahma salts, comprising the recrystallization of Bahma salts in a solvent. The solvent may especially be chosen from acetone, water, methanol, a water/n-propanol azeotrope and mixtures thereof.

The enantiomeric purification process of the present invention may especially be performed after the process for resolving the baclofen enantiomers according to the present invention described above.

The enantiomeric purification process of the present invention is based on the exploitation of the ternary phase diagram comprising the domain of the solid solutions and the solubilities of the system {Solvent—Bahma (R) enantiomer—Bahma (S) enantiomer}, represented in FIG. 7.

This figure shows an isothermal and isobaric section of the ternary phase diagram between the salts of the two Bahma enantiomers and a solvent, the chosen temperature allowing high chiral discrimination between the two enantiomers. Starting with a mixture of salts of Bahma (R) and (S) enantiomers of known composition I, which may especially be a mixture of (R) and (S) enantiomers obtained during the preferential crystallization process according to the present invention, and by adding solvent, various domains constituted of phases each having a different composition and a different nature are traversed:

I→$H_0$: three-phase domain constituted of the two Bahma enantiomers in solid form (ssR and ssS) and of the saturated racemic solution (r.s.s.);

$H_0$→G: two-phase domain constituted of a salt enriched in the Bahma (R) enantiomer (ssR) in solid form and of its saturated solution (sat.sol.), the proportion of crystals of Bahma (R) enantiomer decreasing throughout the segment [$H_0$G], the point $H_0$ being the point that is the richest in crystals of Bahma (R) enantiomer;

G→F: one-phase domain constituted of an under-saturated solution (U.S.S.).

Thus, by precisely knowing the initial composition of the mixture I and its mass, the solid solution domains and the solubility of the racemic mixture, the composition of the point $H_0$ can be determined with precision, which makes it possible, by filtration, to separate the salt enriched in the Bahma (R) enantiomer in solid form, represented by the point $P_0$, from the saturated racemic solution $L_0$. This point $H_0$ is reached by adding a volume $V_{H0}$ of solvent or a mass $m_{H0}$ of solvent to the mixture I.

It is also possible to add a volume of solvent $V_{H1}$ slightly greater than $V_{H0}$ ($V_{H1}=V_{H0}+\Delta V$) or a mass of solvent $m_{H1}$ slightly greater than $m_{H0}$ ($m_{H1}=m_{H0}+\Delta m$) so as to reach the composition point $H_1$. After filtration, the salt enriched in the Bahma (R) enantiomer in solid form, represented by the point $P_1$, is separated from the saturated racemic solution $L_1$. The addition of this amount of solvent $V_{H1}$ or $m_{H1}$ makes it possible to obtain a salt comprising a higher proportion of Bahma (R) enantiomer than that obtained by adding an amount of solvent $V_{H0}$ or $m_{H0}$. On the other hand, the yield of salt enriched by adding an amount of solvent $V_{H1}$ or $m_{H1}$ is lower than that obtained by adding an amount of solvent $V_{H0}$ or $m_{H0}$ since a larger amount of Bahma (R) enantiomer remains dissolved in the saturated solution. The lower the amount of solvent $\Delta V$ or $\Delta m$, the more limited the amount of Bahma (R) enantiomer which remains dissolved in the saturated solution.

FIG. 7 illustrates the enantiomeric purification process for a mixture initially enriched in Bahma (R) enantiomer, but the process may be applied symmetrically to a mixture enriched in Bahma (S) enantiomer.

Thus, according to a preferred embodiment, the process for the enantiomeric purification of the Bahma salt according to the present invention comprises the following steps:

a) providing a solid mixture of Bahma (R) and (S) enantiomers of known composition represented by the point I on the isothermal and isobaric section of the ternary phase diagram between the two Bahma enantiomers and a solvent;

b) adding an amount of solvent so as to pass into the two-phase domain constituted of a salt enriched in a Bahma enantiomer in solid form and of its saturated solution of said ternary phase diagram;

c) filtering the mixture obtained in step b) to obtain the salt enriched in a Bahma enantiomer.

Preferably, the amount of solvent added in step b) is the volume $V_{H0}$ or the mass $m_{H0}$ of solvent which makes it possible to reach the point $H_0$ on said phase diagram, said point $H_0$ corresponding to the intersection of the curve passing between point I and point F, point F being the peak of the phase diagram corresponding to the pure solvent, and of the curve $P_0$-$L_0$ (i.e. the conode) delimiting the three-phase domain from the two-phase domain of the salt enriched in Bahma enantiomer that it is desired to obtain.

Preferably, the amount of solvent added in step b) is the volume $V_{H1}=V_{H0}+\Delta V$ or the mass $m_{H1}=m_{H0}+\Delta m$ of solvent that makes it possible to reach the point $H_1$ on said phase diagram, said point $H_1$ corresponding to the intersection of the curve passing between point I and point F, point F being the peak of the phase diagram corresponding to the pure solvent, and of the curve $P_1$-$L_1$ (i.e. the conode).

The Bahma salts obtained via the resolution process of the present invention and/or the enantiomeric purification process of the present invention may be transformed into baclofen or into a baclofen salt other than the Bahma salt without racemization, i.e. without loss of enantiomeric excess. The transformation of Bahma salts into baclofen may especially be performed by adding a base.

A subject of the present invention is also a baclofen hydrogen maleate salt of R(-) absolute configuration or a baclofen hydrogen maleate salt as obtained via the processes of the present invention, for its use in the treatment of multiple sclerosis, paralyses or alcohol dependency. Specifically, the baclofen hydrogen maleate salt is pharmaceutically acceptable. Furthermore, the process of the present invention does not generate any byproducts to be eliminated, which makes it possible to use the baclofen hydrogen maleate salt obtained directly via the process described above in the treatment of multiple sclerosis, paralyses or alcohol dependency.

The invention will now be illustrated by the nonlimiting examples that follow.

FIGURES

FIG. 1 is an optical microscopy image of a single crystal with an enantiomeric excess of 98.6% derived from a racemic salt of Bahma prepared in example 1.

FIG. 2 is the binary phase diagram of Bahma obtained by differential scanning calorimetry (DSC) (the liquidus curve is not present, given that the Bahma salt decomposes during or after melting).

Figure 9:
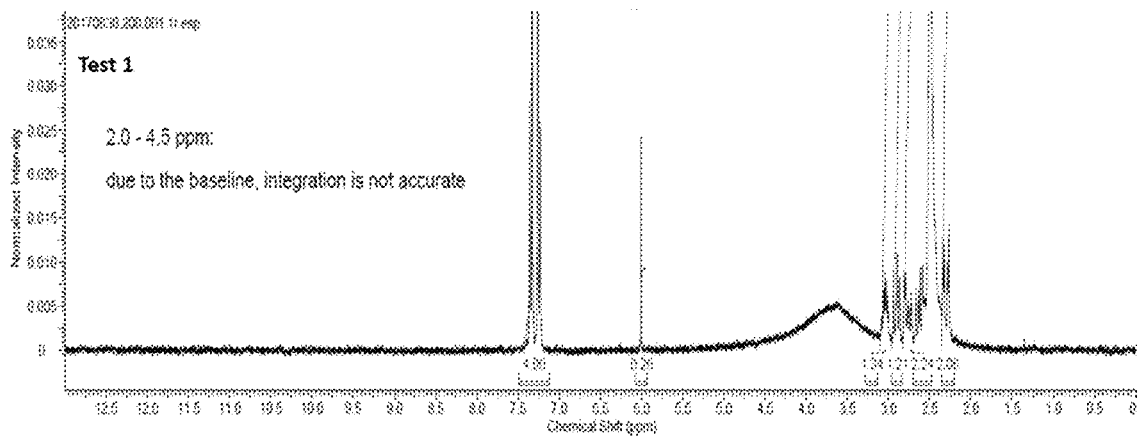

FIG. 9 corresponds to the $^1$H NMR spectrum of Test 1 of example 5 in deuterated DMSO.

Figure 10:
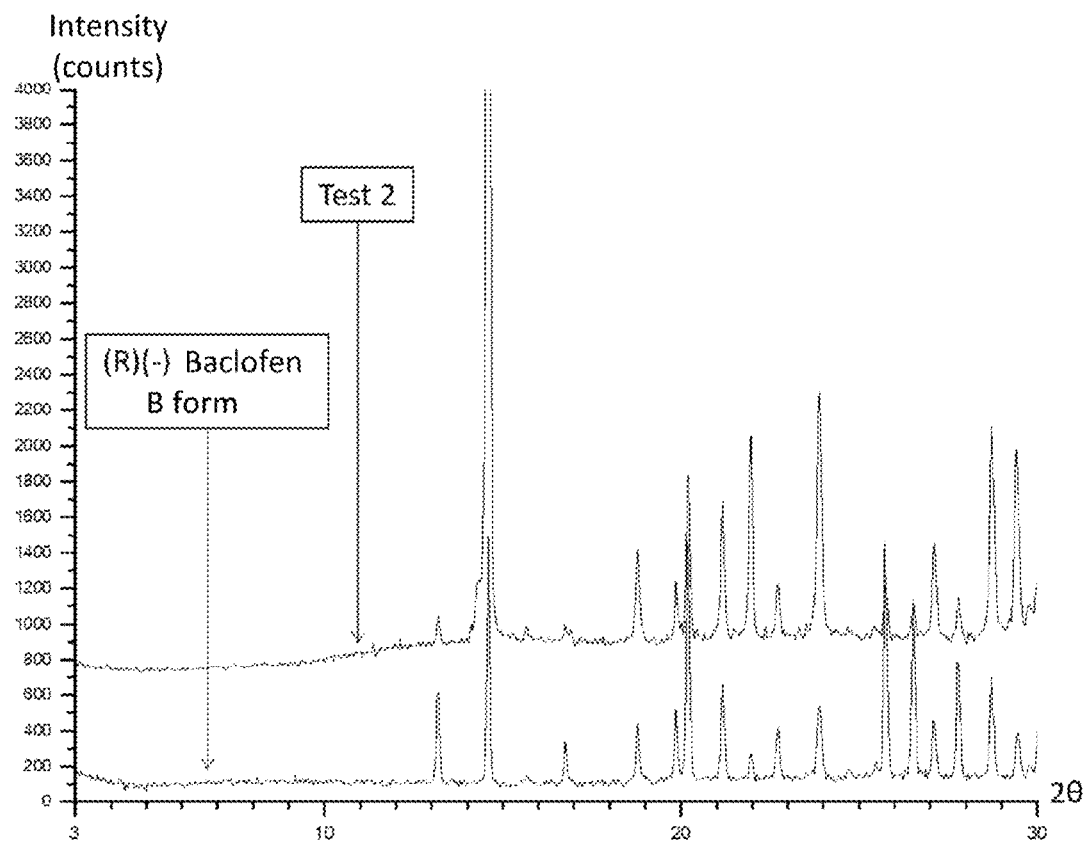

FIG. 10 is a comparison of the diffractograms, obtained by x-ray diffraction analysis, of the B form of (R)(-)-baclofen and of Test 2 of example 5.

Figure 11:
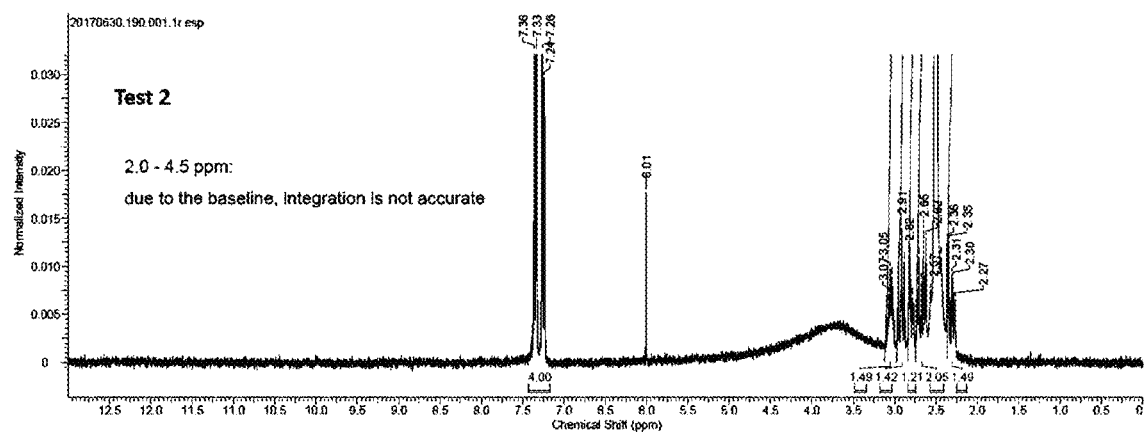

FIG. 11 corresponds to the $^1$H NMR spectrum of Test 2 of example 5 in deuterated DMSO.

Figure 12:
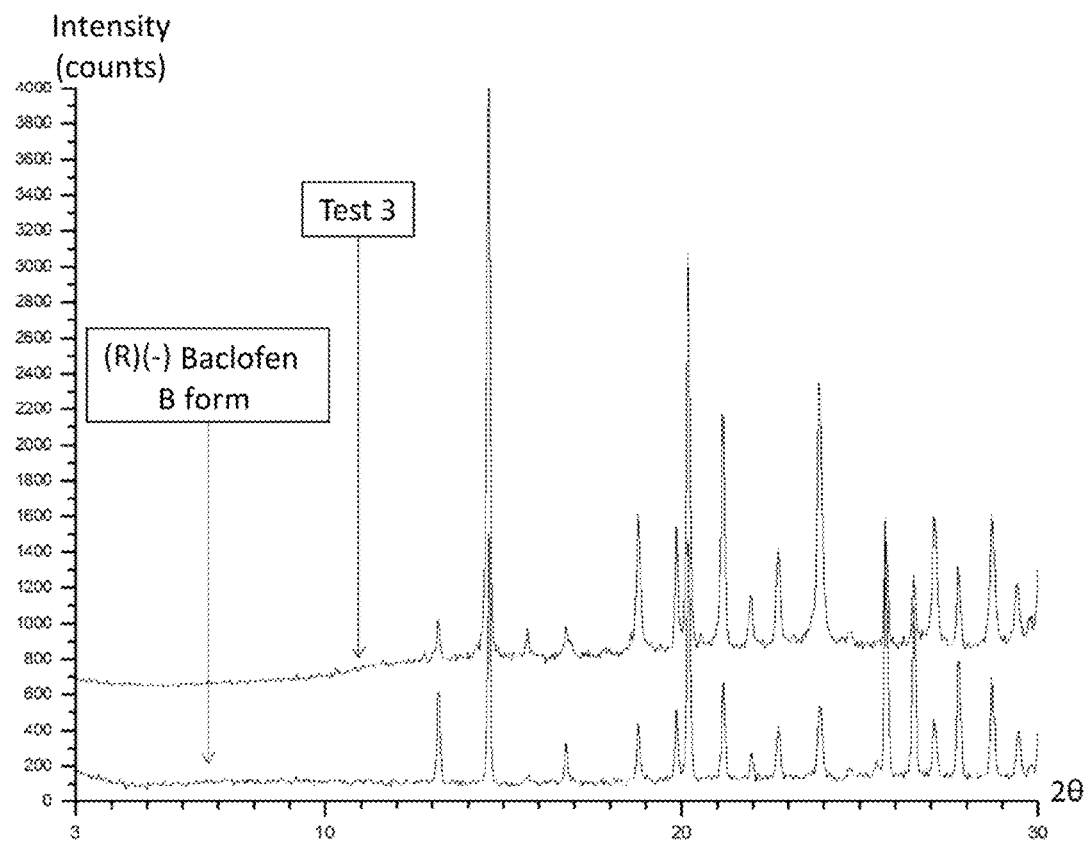

FIG. 12 is a comparison of the diffractograms, obtained by x-ray diffraction analysis, of the B form of (R)(−)-baclofen and of Test 3 of example 5.

Figure 13:
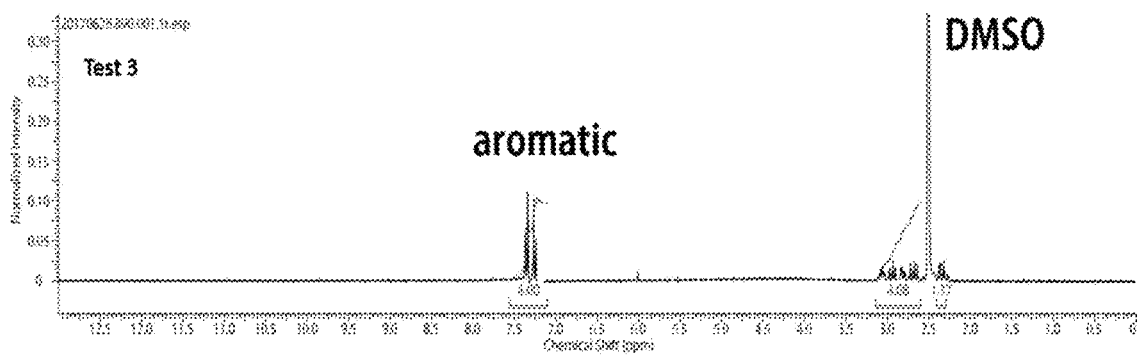

FIG. 13 corresponds to the ¹H NMR spectrum of Test 3 of example 5 in deuterated DMSO.

Figure 14:
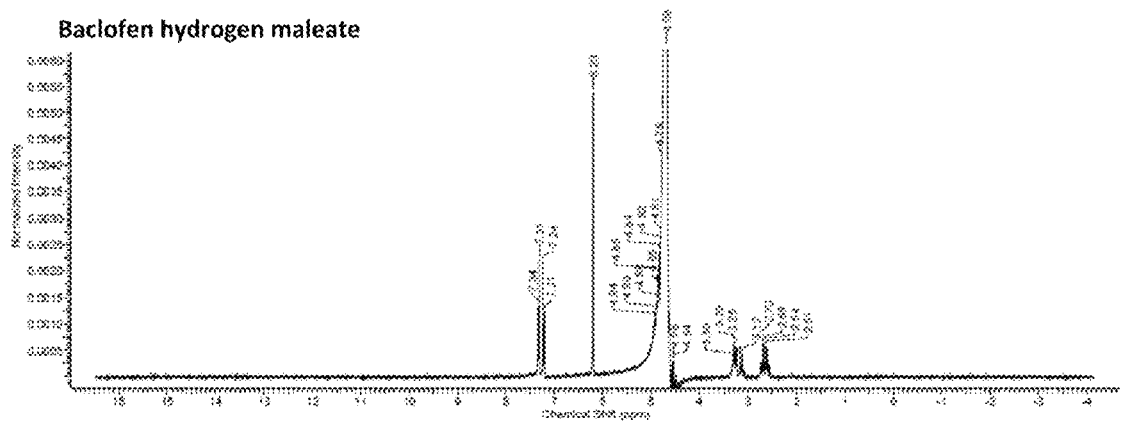

FIG. 14 corresponds to the ¹H NMR spectrum of the baclofen hydrogen maleate salt in deuterated water.

Figure 15:
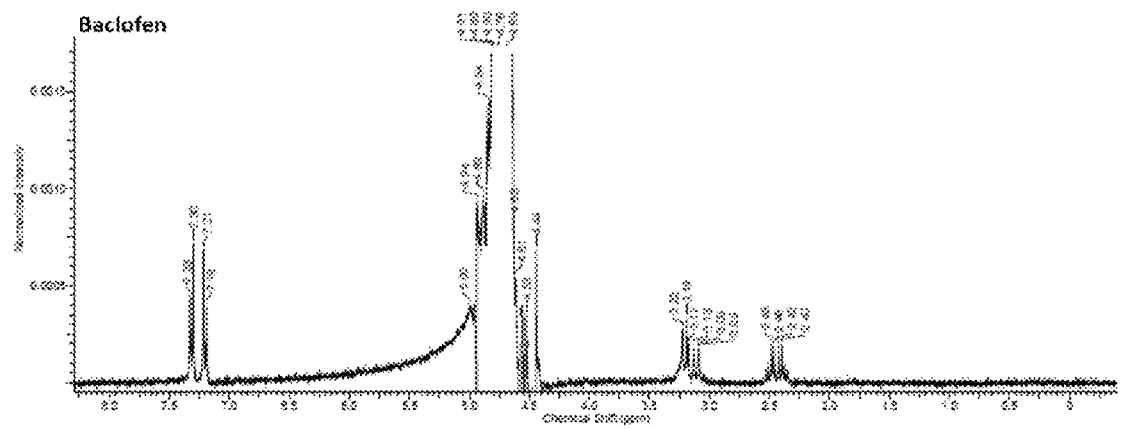

FIG. 15 corresponds to the ¹H NMR spectrum of baclofen in deuterated water.

Figure 16:
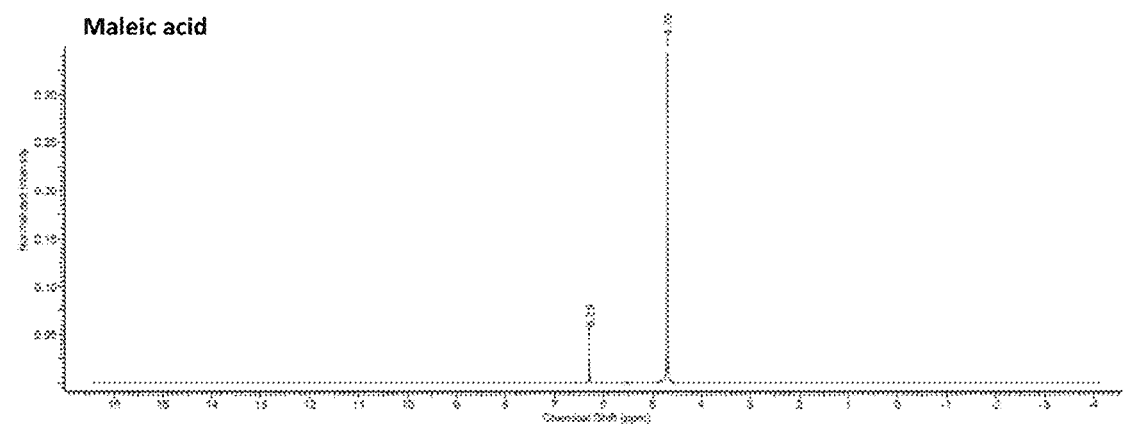

FIG. 16 corresponds to the ¹H NMR spectrum of maleic acid in deuterated water.

ANALYTICAL TECHNIQUES

Determination of the Melting/Decomposition Point and Production of the Binary Phase Diagram by Differential Scanning Calorimetry (DSC)

The differential scanning calorimetry measurements were taken in the following manner:
   DSC 204 F1 Netzsch equipped with an Intracooler
   aluminum crucible, closed aluminum lid
   Atmosphere: helium
   Heating rate: 5K.min⁻¹
   Data processing: Netzsch Proteus Thermal Analysis software (v.4.8.4)

Following the DSC and chiral HPLC analyses performed on single crystals obtained at 20 and 70° C. (98.3% ee at 70° C. and 98.8% ee at 20° C.), the binary phase diagram of FIG. 1 was established. The enantiomeric excess (% ee) was determined by chiral HPLC according to the method described below.

Determination of the Enantiomeric Excess (% ee) by Chiral HPLC

The chromatographic method originates from that described in Hefnawy, M., Aboul-Enein, H. *Talanta*, 2003, vol. 61, No. 5, pages 667-673.

The enantiomeric excesses were determined by chiral HPLC chromatography using a Chirobiotic T column (length 15 cm, inside diameter 4.6 mm, 5 μm particles) mounted on a Spectra System HPLC chain equipped with an AS sample changer, a P1000 pump and a UV1000 detector. The experimental conditions were:
   Solvent: isocratic mixture of methanol, water, acetic acid and triethylamine in 98:2:0.1:0.1 proportions;
   Flow rate: 1 ml.min⁻¹;
   Detector: λ=226 nm;
   Volume injected: 10 μL Determination of the Enantiomeric Excess (% ee) by Polarimetry Between each preferential crystallization, the enantiomeric excesses (% ee) of the precipitates and of the solution were also determined by polarimetry. This technique is faster than chiral HPLC analysis and thus makes it possible to check the correct progress of the resolution process so as to adjust the parameters accordingly (amount of solvent and of racemic Bahma salt to be compensated for before the start of a crystallization).

These analyses were performed on a Perkin-Elmer Model 341 polarimeter equipped with a thermostatically regulated 10 cm measuring cell allowing analysis at various wavelengths. The measurements were taken at 25° C. and the samples were dissolved in the water/n-propanol azeotrope (43.29 mol %). The table below gives the specific optical rotation (α) of a pure Bahma enantiomer at various wavelengths (λ).

| λ (nm) | α (°) |
|---|---|
| 365 | −0.35 |
| 589 | −0.11 |
| 578 | −0.08 |
| 546 | −0.1 |
| 436 | −0.19 |

The wavelength of 365 nm was retained since it had the best deviation of polarized light (−0.35°).

Figure 3:
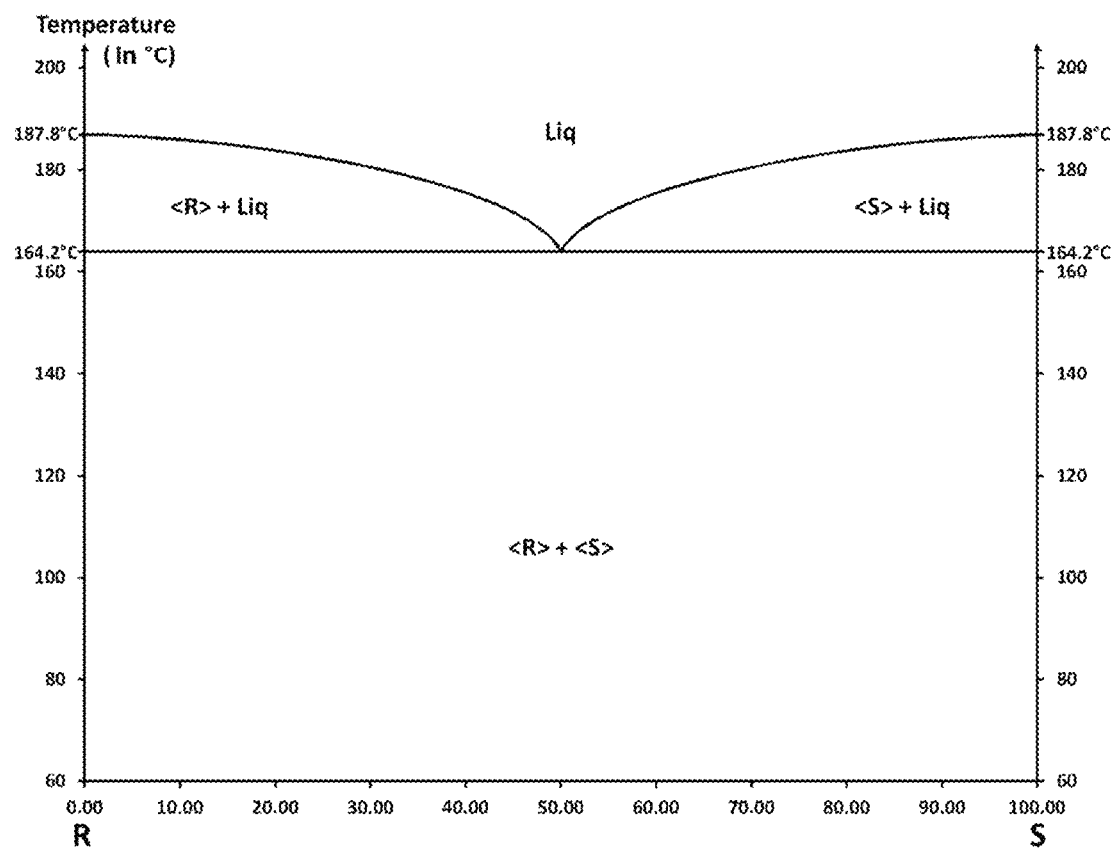
FIG. 3 is a theoretical binary phase diagram of a conglomerate having a partial solid solution.
Figure 4:
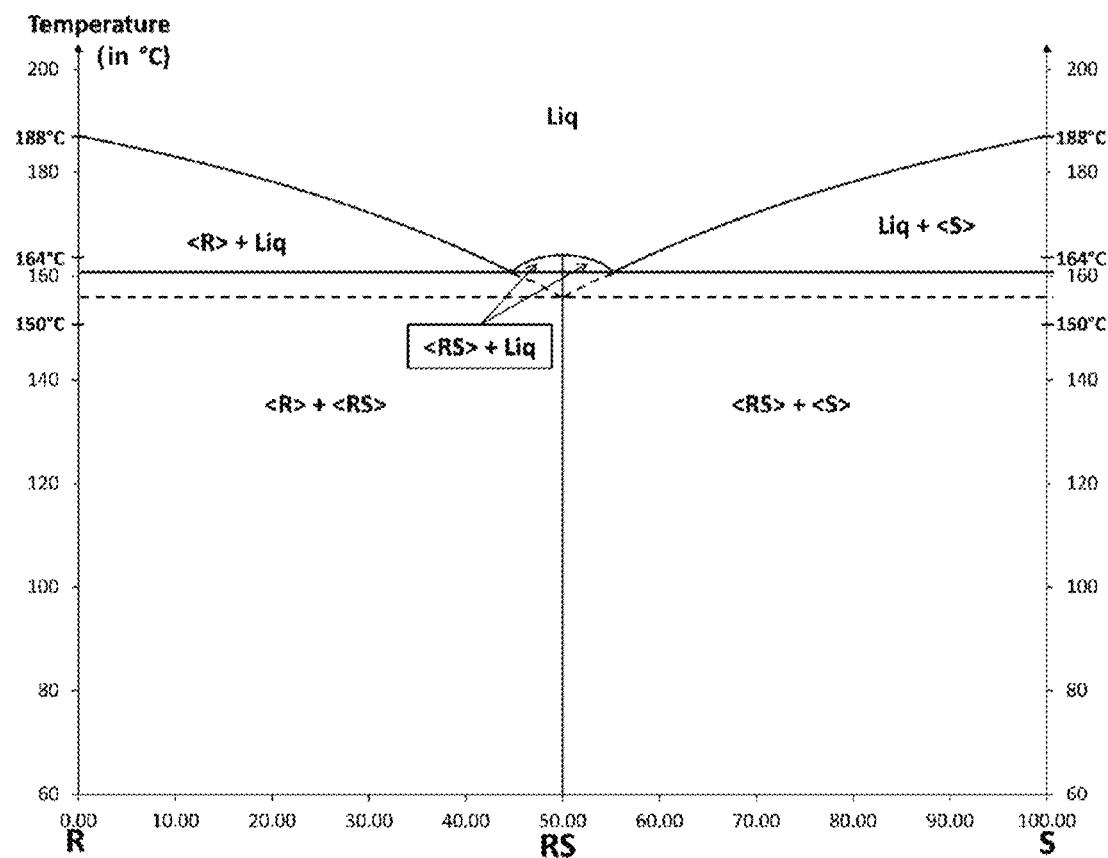
FIG. 4 is a theoretical binary phase diagram of a baclofen salt other than the Bahma salt with the usual presence of a stoichiometric racemic compound.
Figure 5:
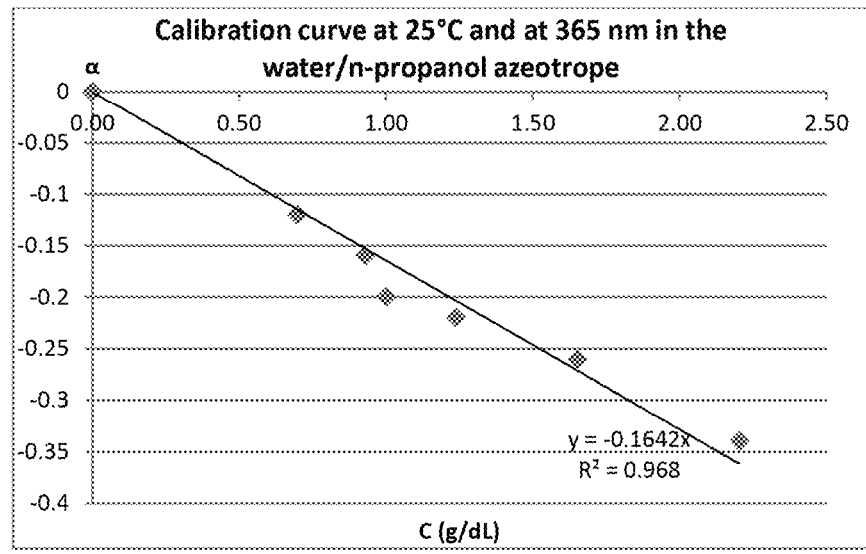
FIG. 5 represents the calibration curve plotted by varying the concentration (C) of a pure Bahma enantiomer and by measuring the specific optical rotation (a) at a wavelength of 365 nm in the water/n-propanol azeotrope at 25° C.

FIG. 5 shows the calibration curve which was plotted by varying the concentration of the pure Bahma enantiomer and by measuring the specific optical rotation at a wavelength of 365 nm. The values are reported in the table below

| C (g/dL) | α (°) |
|---|---|
| 2.20 | −0.34 |
| 1.65 | −0.26 |
| 1.24 | −0.22 |
| 0.93 | −0.16 |
| 0.70 | −0.12 |
| 0.00 | 0 |

It was then possible to deduce the specific optical rotation value for Bahma via the following formula:

$$\alpha = [\alpha]_{365nm}^{25°\,C.} * l * C$$

in which:
α is the optical rotation of the sample in degrees (°);
C is the concentration of the sample in g.dL⁻¹;
l is the length of the analysis cell in dm;
$[\alpha]_{365nm}^{25°\,C.}$ is the specific optical rotation of Bahma at 25° C. and at 365 nm in the solvent used, expressed in °.dL.g⁻¹.dm⁻¹.

The specific optical rotation of Bahma under these conditions is 0.1642°dL.g⁻¹.dm⁻¹.

Analysis by Single-Crystal X-Ray Diffraction

The single crystal chosen was bonded to the end of a glass rod and mounted on a goniometric head of the Brüker SMART APEX diffractometer equipped with a two-dimensional detector. Three sets of measurements were recorded (in total 1800 images (frames)) corresponding to 3 ω scans (incrementation of 0.3°), for four different values of φ.

The elemental lattice parameters and the orientation matrix were determined using the SMART program. The data integrations and the refinement of the lattice parameters were performed using the SAINT program. The intensities were corrected for the Lorentz polarization factor and for absorption by the SAINT and SADABS programs to obtain the $F_O^2$.(hkl). The WinGX program was used for determination of the space group, the resolution of the structure and its refinement.

Analysis by Powder X-Ray Diffraction

The powder x-ray diffraction analyses were performed with a D8 Discover diffractometer (Brüker). The instrument is equipped with an x-ray tube containing a copper anticathode (40 kV, 40 mA, radiation Kα1=1.5406 Å, radiation Kα2=1.5444 Å) and is mounted with a Lynx eye angular detector. The analysis program used is a 3 to 30° sweep in 2θ in increments of 0.04° with 0.5 s/step and a rotation of 20 rpm (Phi spinner).

Determination of the Solubility

The solubility of a Bahma salt in a given solvent was calculated, for a given temperature and in a given volume of solvent, via the following formula:

$$\frac{m_{Bahma}}{m_{Bahma} + (\rho_{solvent} \times V_{solvent})} \times 100$$

in which $m_{Bahma}$ is the mass of the Bahma salt introduced in grams to reach saturation;

$\rho_{solvent}$ is the density of the solvent in g.mL$^{-1}$; and $V_{solvent}$ is the volume of the solvent in mL.

Experimental Device for Resolution by Preferential Crystallization

The crystallizations were performed in closed tubes (diameter 3 cm, length 9 cm). Stirring was performed by cruciform magnetic bars and the temperature control was provided by a Lauda ECO RE 415 programmable cryothermostat.

The entrainments were performed by means of the AS3PC process described in patent application WO 1995/008522.

In the course of the entrainments, samples of solutions (10 µL diluted in 1 mL of mobile phase) were collected so as to determine their enantiomeric excess by chromatography according to the method described above.

a) First Crystallization

A volume V of 40 mL of saturated solution of racemic Bahma salt at 50° C. (temperature $T_L$) in a solvent or a solvent mixture was prepared by filtration of a suspension at this same temperature after an equilibration time of several hours to reach saturation.

At least 5% by weight of excess of a pure Bahma enantiomer (Bahma-100% ee) relative to the weight of the racemic Bahma salt (rac. Bahma) introduced are added to this clear solution. The suspension obtained is then overheated slightly to a temperature $T_B=T_L+3°$ C. Thus, all the seeds of the enantiomer in deficit that might remain at $T_L$ are necessarily dissolved. The starting system is thus a suspension of the enantiomer in excess. The liquid phase of the suspension is saturated in one enantiomer and slightly under-saturated in the other enantiomer. This system has the advantage of being at thermodynamic equilibrium.

A cooling temperature ramp is then applied to the system from $T_B$ to $T_F$ ($T_F<T_B$), the final temperature at which the system is rapidly filtered without waiting for the thermodynamic equilibrium to be established.

b) Following Crystallizations

At the end of each entrainment, the suspensions were filtered through a sinter funnel. A sample of the filtrates (10 µL of filtrate diluted in 1 mL of mobile phase) was recovered for analysis of the % ee by chiral HPLC and the remainder was set aside to perform the following entrainment. The solid recovered was weighed and 15 mg were then dissolved in 1.5 mL of water/n-propanol azeotrope for analysis of the % ee by polarimetry and 10 µL of this solution were diluted in 1 mL of mobile phase for analysis of the % ee by chiral HPLC.

The filtrate recovered was compensated by adding a mass of racemic Bahma salt substantially equal to that of the crystals recovered in the preceding crystallization. The filtrate was also compensated for the losses of solvent by adding solvent to make up to 40 mL (initial volume of solvent).

The system was then heated again to $T_B$ at which point a new suspension was obtained. After 30 minutes of equilibration at this temperature, the same cooling program was applied, at the end of which a new filtration gives the opposite enantiomer to the preceding one. Successive recycling makes it possible to recover the same enantiomer as the starting one following the odd crystallizations, whereas the other enantiomer is systematically recovered for all the even crystallizations.

By successive recycling, it is then possible to preparatively resolve the two enantiomers of a racemic mixture.

Examples

Example 1: Preparation and Characterization of Bahma Salts

The Bahma salts (racemic or enantiomerically pure) used in the process of the present invention were prepared by evaporation of a suspension of baclofen (racemic or enantiomerically pure) and of maleic acid (1:1 stoichiometric mixture) in acetone.

The single crystals of Bahma salt for the x-ray diffraction analysis were obtained by dissolving 50 mg of racemic Bahma salt in a given volume of solvent: water, methanol or water/n-propanol azeotrope (to achieve a homogeneous solution, the mixture may be heated). After dissolution of the solids, a temperature may be imposed on the solution or it is left at room temperature (about 20° C.). The salt crystals highly enriched in Bahma form by evaporation of the solvent or solvent mixture after a few days for the slowest evaporations; single crystals were thus obtained by evaporation of solutions left at 20, 50 and 70° C.

These single crystals were studied by x-ray diffraction to determine their complete structure. The crystallographic data for a single crystal obtained at 20° C. are reported in table 1.

TABLE 1

| System | Monoclinic |
|---|---|
| Space group | P2$_1$ (No. 4) |
| a/Å | 5.728(1) |
| b/Å | 13.774(1) |
| c/Å | 9.618(9) |
| α/° | 90 |
| β/° | 106.628(1) |
| γ/° | 90 |
| Volume/Å$^3$ | 727.2(2) |
| Final R$_1$ (I > 2σ(I)) | 0.0287 |
| Final wR(F$^2$) (I > 2σ(I)) | 0.0812 |
| Final R$_1$ | 0.0294 |
| Final wR(F$^2$) | 0.0817 |
| Flack parameter | −0.02(5) |

$R_1 = \Sigma(||F_O| - |F_C||)/\Sigma|F_O|$
$wR(F^2) = [\Sigma[w(F_O^2 - F_C^2)^2]/\Sigma[w(F_O^2)^2]]^{1/2}$ The space group, the number of molecules in the asymmetric unit, the absence of disorder and the value of the Flack parameter indicate virtually total chiral discrimination in the solid state at room temperature. These observations were correlated by identical behavior up to at least 70° C.

Table 2 below shows the reduced coordinates of the atoms other than hydrogen ($\times 10^4$) and the isotropic agitation factor $U_{eq}$ (Å$^2 \times 10^3$).

TABLE 2

| Atom | x | y | | $U_{eq}$ |
|---|---|---|---|---|
| C(1) | −5631(3) | 8817(1) | −938(2) | 33(1) |
| C(2) | −3549(3) | 9419(1) | −1112(2) | 35(1) |
| C(3) | −3199(3) | 10379(1) | −272(2) | 31(1) |
| C(4) | −1434(3) | 10998(1) | −828(2) | 36(1) |
| C(5) | −2316(3) | 10237(1) | 1357(2) | 30(1) |
| C(6) | −80(3) | 9806(1) | 2015(2) | 37(1) |
| C(7) | 739(3) | 9687(1) | 3512(2) | 39(1) |

TABLE 2-continued

| Atom | x | y | | $U_{eq}$ |
|---|---|---|---|---|
| C(8) | −725(4) | 9994(1) | 4340(2) | 39(1) |
| C(9) | −2951(3) | 10412(1) | 3718(2) | 41(1) |
| C(10) | −3730(3) | 10535(1) | 2229(2) | 35(1) |
| Cl(1) | 289(1) | 9851(1) | 6215(1) | 58(1) |
| N(1) | −1225(3) | 12006(1) | −269(2) | 38(1) |
| O(1) | −7139(2) | 9107(1) | −380(2) | 46(1) |
| O(2) | −5825(2) | 7935(1) | −1485(1) | 39(1) |
| C(1A) | 2665(3) | 2546(1) | 3835(2) | 35(1) |
| O(1A) | 2173(2) | 2425(1) | 2502(1) | 41(1) |
| O(2A) | 4794(3) | 2762(2) | 4591(2) | 67(1) |
| C(2A) | 683(3) | 2437(1) | 4532(2) | 35(1) |
| C(3A) | 787(3) | 2427(2) | 5927(2) | 37(1) |
| C(4A) | 2891(4) | 2502(2) | 7252(2) | 40(1) |
| O(3A) | 5022(3) | 2668(2) | 7127(2) | 62(1) |
| O(4A) | 2565(3) | 2399(1) | 8443(2) | 60(1) |

Table 3 below shows the reduced coordinates of the hydrogen atoms ($\times 10^4$) and the isotropic agitation factor $U_{eq}$ ($Å^2 \times 10^3$).

TABLE 3

| Atom | x | y | | $U_{eq}$ |
|---|---|---|---|---|
| H(2A) | −3817 | 9558 | −2133 | 41 |
| H(2B) | −2063 | 9042 | −787 | 41 |
| H(3) | −4770 | 10714 | −506 | 38 |
| H(4A) | 161 | 10697 | −542 | 43 |
| H(4B) | −1985 | 11014 | −1880 | 43 |
| H(6) | 883 | 9593 | 1445 | 44 |
| H(7) | 2245 | 9406 | 3947 | 47 |
| H(9) | −3924 | 10610 | 4290 | 49 |
| H(10) | −5231 | 10823 | 1806 | 42 |
| H(1A) | −2693 | 12278 | −496 | 56 |
| H(1B) | −260 | 12345 | −665 | 56 |
| H(1C) | −598 | 11999 | 690 | 56 |
| H(2) | −4657 | 7823 | −1791 | 58 |
| H(2A1) | −867 | 2364 | 3894 | 42 |
| H(3A) | −713 | 2362 | 6108 | 44 |
| H(3A1) | 4939 | 2737 | 6267 | 93 |

Figure 6:
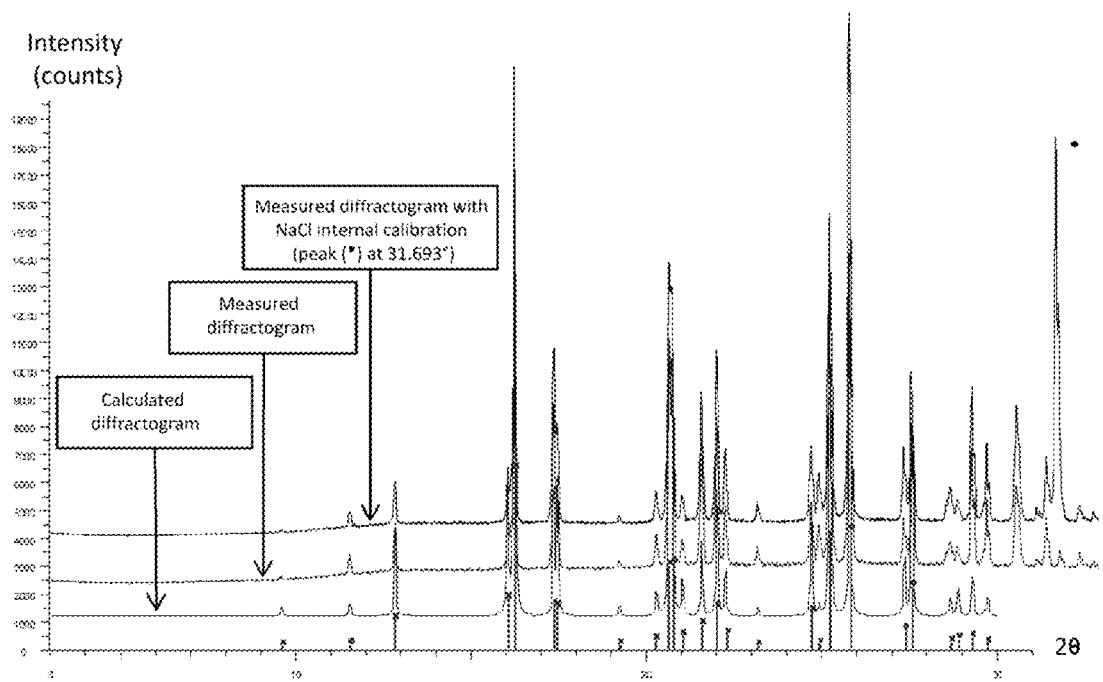
FIG. 6 represents the XRD diffractogram calculated and measured for the racemic salt of Bahma of example 1.
Figure 7:
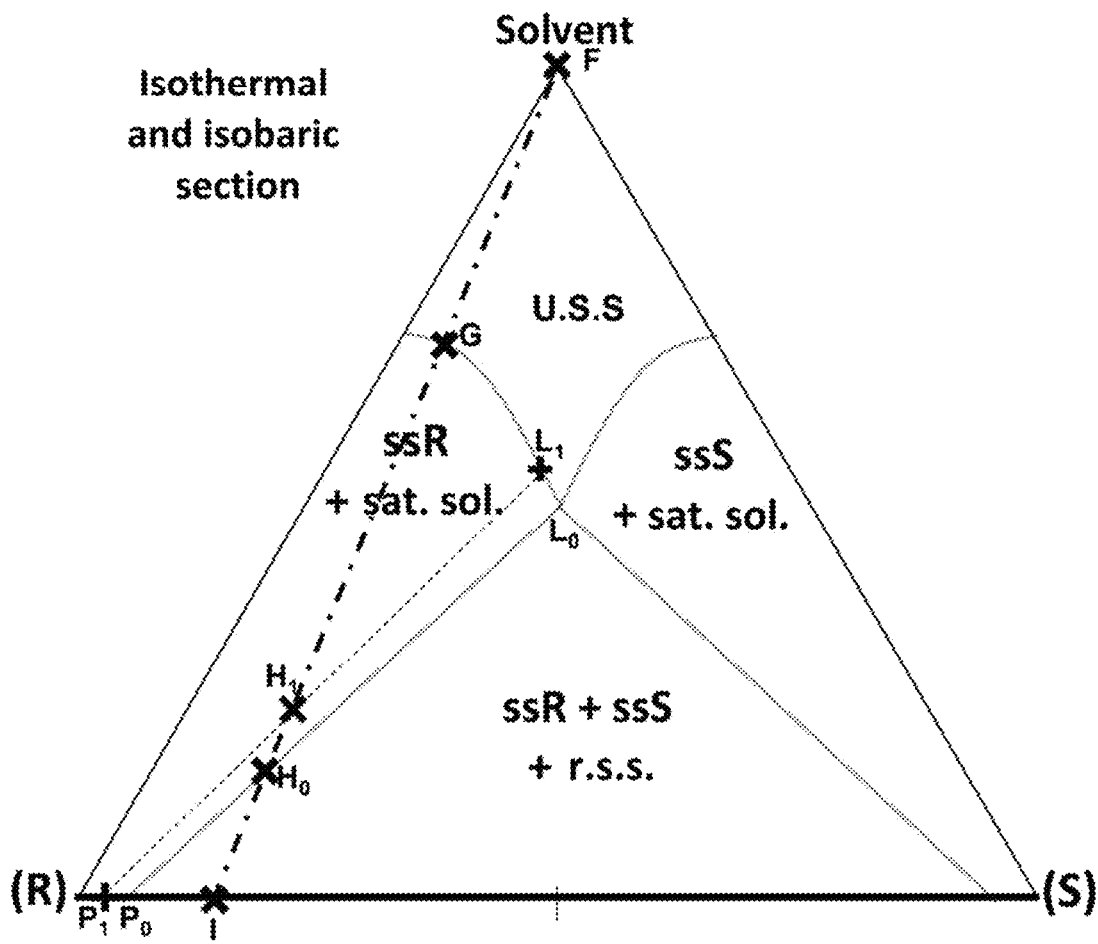
FIG. 7 represents the ternary isobaric isotherm of the system {Bahma (R) enantiomer—Bahma (S) enantiomer—Solvent} illustrating the enantiomeric purification process of the present invention.

Table 4 below shows the calculated and measured position and intensity of the characteristic XRD peaks for the racemic Bahma salt. The corresponding XRD diffractograms are shown in FIG. 6.

TABLE 4

| Miller indices | | | Calculated Bahma | | | Measured Bahma | | | |
|---|---|---|---|---|---|---|---|---|---|
| | | | 2θ/ | | | 2θ/ | | | Intensity |
| h | k | l | deg | d/Å | I/rel. | deg | d/Å | (counts) | (I/Io %) |
| 0 | 0 | 1 | 9.59 | 9.22 | 2.41 | 9.58 | 9.223 | 344 | 1.8 |
| 0 | 1 | 1 | 11.54 | 7.66 | 2.72 | 11.51 | 7.679 | 1116 | 5.8 |
| 0 | 2 | 0 | 12.83 | 6.89 | 5.77 | 12.81 | 6.904 | 2266 | 11.8 |
| 0 | 2 | 1 | 16.04 | 5.52 | 4.96 | 16.03 | 5.525 | 2047 | 10.6 |
| 1 | 0 | 0 | 16.12 | 5.49 | 5.4 | | | | |
| −1 | 0 | 1 | 16.24 | 5.45 | 54.44 | 16.21 | 5.462 | 8893 | 46.2 |
| 1 | 1 | 0 | 17.36 | 5.1 | 33.95 | 17.35 | 5.108 | 6557 | 34 |
| −1 | 1 | 1 | 17.47 | 5.07 | 19.97 | 17.45 | 5.078 | 3944 | 20.5 |
| 0 | 1 | 2 | 20.3 | 4.37 | 6.49 | 20.28 | 4.375 | 1874 | 9.7 |
| 1 | 2 | 0 | 20.66 | 4.3 | 51.05 | 20.64 | 4.3 | 8915 | 46.3 |
| −1 | 2 | 1 | 20.75 | 4.28 | 44.13 | 20.7 | 4.288 | 8204 | 42.6 |
| 1 | 0 | 1 | 21.04 | 4.22 | 3.14 | 21.02 | 4.224 | 1696 | 8.8 |
| 0 | 3 | 1 | 21.59 | 4.11 | 22.72 | 21.56 | 4.119 | 5218 | 27.1 |
| 1 | 1 | 1 | 22.02 | 4.03 | 29.17 | 21.99 | 4.039 | 6216 | 32.3 |
| −1 | 1 | 2 | 22.28 | 3.99 | 17.94 | 22.24 | 3.993 | 2895 | 15 |
| 0 | 2 | 2 | 23.2 | 3.83 | 2.46 | 23.16 | 3.837 | 1381 | 7.2 |
| 1 | 2 | 1 | 24.72 | 3.6 | 14.87 | 24.69 | 3.603 | 3047 | 15.8 |
| −1 | 2 | 2 | 24.95 | 3.57 | 13.08 | 24.92 | 3.57 | 2218 | 11.5 |

TABLE 4-continued

| Miller indices | | | Calculated Bahma | | | Measured Bahma | | | |
|---|---|---|---|---|---|---|---|---|---|
| | | | 2θ/ | | | 2θ/ | | | Intensity |
| h | k | l | deg | d/Å | I/rel. | deg | d/Å | (counts) | (I/Io %) |
| 1 | 3 | 0 | 25.24 | 3.53 | 78.2 | 25.22 | 3.528 | 9331 | 48.4 |
| −1 | 3 | 1 | 25.32 | 3.51 | 7.46 | | | | |
| 0 | 4 | 0 | 25.82 | 3.45 | 100 | 25.79 | 3.452 | 19184 | 100 |
| 0 | 3 | 2 | 27.38 | 3.25 | 11.56 | 27.35 | 3.258 | 2470 | 12.8 |
| 0 | 4 | 1 | 27.61 | 3.23 | 34.09 | 27.57 | 3.233 | 5707 | 29.6 |
| 1 | 0 | 2 | 28.6 | 3.12 | 2.89 | 28.55 | 3.124 | 1238 | 6.4 |
| 1 | 3 | 1 | 28.7 | 3.11 | 6.3 | 28.68 | 3.11 | 1618 | 8.4 |
| −1 | 3 | 2 | 28.9 | 3.09 | 4.41 | 28.87 | 3.09 | 1396 | 7.2 |
| −1 | 0 | 3 | 28.93 | 3.08 | 2.51 | | | | |
| 1 | 1 | 2 | 29.34 | 3.04 | 27.72 | 29.29 | 3.047 | 5113 | 26.5 |
| −1 | 1 | 3 | 29.66 | 3.01 | 4.39 | | | | |
| 0 | 1 | 3 | 29.77 | 3 | 17.51 | 29.71 | 3.005 | 3125 | 16.2 |

Example 2: Resolution in the n-Propanol/Water Azeotropic Mixture by Auto-Seeded Preferential Crystallization The solubility of the racemic Bahma salt at various temperatures was determined in the n-propanol/water azeotropic mixture ($\rho = 0.870$ g.mL$^{-1}$). The calculated values are presented in the table below.

| Temperature | Solubility |
|---|---|
| 20° C. | 1.49% |
| 35° C. | 2.80% |
| 50° C. | 4.81% |

Several entrainments were performed in this solvent using a saturated racemic solution at 50° C. and following the experimental device described previously.

1$^{st}$ Series:

Initial system: 40 mL saturated at 50° C. (1.7583 g of rac. Bahma in 34.796 g of solvent) and 0.2505 g of Bahma-100% ee

| | Temperature (° C.) | Time (min) | Solution ee (%) | Crude harvests | |
|---|---|---|---|---|---|
| | | | | Mass (g) | ee (%) |
| Test 1 | 53 | 0 | −4.71 | | |
| | 50 | 6 | −4.44 | | |
| | 45 | 16 | −0.40 | | |
| | 40 | 26 | 4.54 | | |
| | 35 | 36 | 11.69 | | |
| | 32.5 | 41 | 15.30 | | |
| | 30 | 46 | 19.92 | 0.6682 g | −91.08 |
| 4 h at 53° C. | | | Compensation 0.6895 g of rac. Bahma and 2 mL of solvent | | |
| Test 2 | 53 | 0 | 6.43 | | |
| | 35 | 36 | −9.89 | | |
| | 30 | 46 | −18.08 | 0.6587 g | +84.29 |
| 12 h at 53° C. | | | Compensation 0.6718 g of rac. Bahma and 2 mL of solvent | | |
| Test 3 | 53 | 0 | −5.47 | | |
| | 35 | 36 | −3.37 | | |
| | 30 | 46 | 10.02 | 0.4971 g | −91.03 |

| Initial system: 40 mL saturated at 50° C. (1.7583 g of rac. Bahma in 34.796 g of solvent) and 0.2505 g of Bahma-100% ee | | | | | |
|---|---|---|---|---|---|
| 2 h at 53° C. | | | Compensation 0.4955 g of rac. Bahma and 2 mL of solvent | | |
| Test 4 | 53 | 0 | 5.14 | | |
|  | 35 | 36 | −2.38 | | |
|  | 30 | 46 | −11.27 | 0.4156 g | +82.72 |
| 1 h at 53° C. | | | Compensation 0.4153 g of rac. Bahma | | |
| Test 5 | 53 | 0 | −3.07 | | |
|  | 35 | 36 | 12.84 | | |
|  | 30 | 46 | 20.93 | 0.5608 g | −93.78 |
| 30 min at 53° C. | | | Compensation 0.555 g of rac. Bahma and 1.5 mL of solvent | | |
| Test 6 | 53 | 0 | 9.76 | | |
|  | 35 | 36 | −5.35 | | |
|  | 30 | 46 | −13.76 | 0.5339 g | +96.59 |

$2^{nd}$ Series:

| Initial system: 40 mL saturated at 50° C. (1.7583 g of rac. Bahma in 34.796 g of solvent) and 0.2445 g de Bahma-100% ee | | | | | |
|---|---|---|---|---|---|
| | | | | Crude harvests | |
| | Temperature (° C.) | Time (min) | Solution ee (%) | Mass (g) | ee (%) |
| Test 1 | 53 | 0 | −11.88 | | |
|  | 35 | 36 | −3.47 | | |
|  | 30 | 46 | 9.75 | 0.5012 g | −94.04% |
| 60 min at 53° C. | | | Compensation 0.5120 g of rac. Bahma and 1.2 mL of solvent | | |
| Test 2 | 53 | 0 | 5.70 | | |
|  | 35 | 36 | −9.90 | | |
|  | 30 | 46 | −17.87 | 0.4679 g | +84.61% |
| 30 min at 53° C. | | | Compensation 0.4621 g of rac. Bahma and 1 mL of solvent | | |
| Test 3 | 53 | 0 | −8.86 | | |
|  | 35 | 36 | 6.62 | | |
|  | 30 | 46 | 15.26 | 0.5496 g | −95.07% |
| 30 min at 53° C. | | | Compensation 0.5469 g of rac. Bahma and 1.5 mL of solvent | | |
| Test 4 | 53 | 0 | 8.16 | | |
|  | 35 | 36 | −8.64 | | |
|  | 30 | 46 | −17.34 | 0.6465 g | +92.52% |
| 30 min at 53° C. | | | Compensation 0.5122 g of rac. Bahma and 1.5 mL of solvent | | |
| Test 5 | 53 | 0 | −8.02 | | |
|  | 35 | 36 | 9.69 | | |
|  | 30 | 46 | 19.47 | 0.6463 g | −88.51% |
| 30 min at 53° C. | | | Compensation 0.5136 g of rac. Bahma and 1.75 mL of solvent | | |
| Test 6 | 53 | 0 | 11.09 | | |
|  | 35 | 36 | −5.15 | | |
|  | 30 | 46 | −17.59 | 0.6124 g | +91.71% |

| Initial system: 40 mL saturated at 50° C. (1.7583 g of rac. Bahma in 34.796 g of solvent) and 0.2445 g de Bahma-100% ee | | | | | |
|---|---|---|---|---|---|
| 30 min at 53° C. | | | Compensation 0.4975 g of rac. Bahma and 1.5 mL of solvent | | |
| Test 7 | 53 | 0 | −12.35 | | |
|  | 35 | 36 | −2.47 | | |
|  | 30 | 46 | 12.65 | 0.5378 g | −91.71% |
| 30 min at 53° C. | | | Compensation 0.5306 g of rac. Bahma and 2 mL of solvent | | |
| Test 8 | 53 | 0 | 7.46 | | |
|  | 35 | 36 | −4.89 | | |
|  | 30 | 46 | −14.73 | 0.5254 g | +88.90% |
| 30 min at 53° C. | | | Compensation 0.5238 g of rac. Bahma and 0.5 mL of solvent | | |
| Test 9 | 53 | 0 | −6.25 | | |
|  | 35 | 36 | 10.26 | | |
|  | 30 | 46 | 19.42 | 0.6444 g | −89.51% |
| 30 min at 53° C. | | | Compensation 0.5183 g of rac. Bahma and 1 mL of solvent | | |
| Test 10 | 53 | 0 | 8.00 | | |
|  | 35 | 36 | −7.59 | | |
|  | 30 | 46 | −16.49 | 0.7194 g | +87.05% |

Example 3: Resolution in Acidified Water by Auto-Seeded Preferential Crystallization The solubility of the racemic Bahma salt at various temperatures was determined in pure water ($\rho=1$ g.mL$^{-1}$), in aqueous 1M HCl solution ($\rho=1.017$ g.mL$^{-1}$) and in aqueous 2M HCl solution ($\rho=1.030$ g.mL$^{-1}$). The calculated values are presented in the table below.

| Temperature | Solubility Water | Solubility 1M HCl | Solubility 2M HCl |
|---|---|---|---|
| 20° C. | 0.75% | 4.51% | 6.48% |
| 35° C. | 1.00% | 6.86% | 11.44% |
| 50° C. | 1.78% | 12.54% | 22.24% |

Thus, the use of an acidified aqueous solution advantageously makes it possible to increase the solubility of the racemic Bahma salt, which makes it possible to improve the productivity of the preferential crystallization. For HCl concentrations of 1M and 2M at these temperatures, the solid phases do not contain any hydrochloride.

Entrainment was performed in 1M HCl using a saturated racemic solution at 50° C. and following the experimental device described previously.

| Initial system: 40 mL saturated at 50° C. (5.8326 g of rac. Bahma and 40.68 g of 1M HCl) and 0.1735 g of Bahma-100% ee | | | | | |
|---|---|---|---|---|---|
| | | | | Crude harvests | |
| | Temperature (° C.) | Time (min) | Solution ee (%) | Mass (g) | ee (%) |
| Test 1 | 50.25 | 0 | −2.89 | | |
|  | 47.5 | 6 | −2.81 | | |
|  | 45 | 11 | −2.03 | | |

-continued

Initial system: 40 mL saturated at 50° C. (5.8326 g of
rac. Bahma and 40.68 g of 1M HCl) and 0.1735 g of Bahma-100% ee

| | | | Crude harvests | |
|---|---|---|---|---|
| Temperature (° C.) | Time (min) | Solution ee (%) | Mass (g) | ee (%) |
| 42.5 | 16 | −0.90 | | |
| 40 | 21 | 3.76 | | |
| 37.5 | 26 | 11.55 | 0.8885 | −90.56% |

Entrainment was performed in 2M HCl using a saturated racemic solution at 50° C. and following the experimental device described previously.

Initial system: 40 mL saturated at 50° C. (11.7835 g of rac. Bahma in 41.2 g of 2M HCl) and 0.2501 g of Bahma-100% ee

| | Tempera-ture (° C.) | Time (min) | Solution ee (%) | Crude harvests | |
|---|---|---|---|---|---|
| | | | | Mass (g) | ee (%) |
| Test 1 | 50.5 | 0 | −3.53 | | |
| | 47.5 | 6 | −2.66 | | |
| | 45.0 | 11 | −2.09 | | |
| | 42.5 | 16 | −5.98 | | |
| | 40.0 | 21 | 3.74 | | |
| | 37.5 | 26 | 10.52 | 1.7437 g | −89.94% |
| 60 min at 50.5° C. | | | Compensation: 1.7457 g of rac. Bahma and 2 mL of 2M HCl | | |
| Test 2 | 50.5 | 0 | / | | |
| | 40.0 | 21 | −2.77 | | |
| | 37.5 | 26 | −11.80 | 2.1713 g | +98.37% |

Example 4: Enantiomeric Purification Process According to the Invention

The enantiomeric purification process according to the invention was performed using 0.4239 g of Bahma salt at −50.43% ee, i.e. a mixture of 0.2138 g of (R)-Bahma and 0.2101 g of racemic Bahma mixture, to which a mass of 27.0787 g of water ($m_{H_2O}$=26.7258 g of water, i.e. an excess Δm=1.32% of water) was added.

The system was then left under magnetic stirring at 20° C. overnight and the suspension was filtered.

The solid was then washed twice with water and the harvest was thus able to be analyzed. 0.1905 g of solid (R)-Bahma salt at −98.59% ee is obtained and the filtrate has a measured purity of −11.56% ee.

Example 5: Process for Obtaining Pure Baclofen from Baclofen Hydrogen Maleate Salt 1 g of enantiomerically pure baclofen hydrogen maleate salt (corresponding to a mass of 0.6480 g of baclofen and 0.3520 g of maleic acid) is dissolved in 10 ml of 1M NaOH solution at 25° C. with stirring.

The pH of the solution is then adjusted by adding a known volume of 37 mass % hydrochloric acid solution. The temperature is controlled in parallel. The addition of hydrochloric acid entrains the precipitation of the B form of baclofen, which is then filtered off, dried, weighed and analyzed by x-ray diffraction and by NMR (nuclear magnetic resonance) analysis.

Three tests were then performed in order to check that the process is viable at various final pH values and various temperatures.

Test 1:

| Test | Volume of HCl added | Final temperature | Final pH | Mass harvested |
|---|---|---|---|---|
| Test 1 | 230 μL | 25° C. | 9.02 | 0.5485 g |

Test 2:

| Test | Volume of HCl added | Final temperature | Final pH | Mass harvested |
|---|---|---|---|---|
| Test 2 | 320 μL | 25° C. | 7.90 | 0.5546 g |

Test 3:

| Test | Volume of HCl added | Final temperature | Final pH | Mass harvested |
|---|---|---|---|---|
| Test 3 | 240 μL | 10° C. | 9.29 | 0.5786 g |

For each of the tests, x-ray diffraction analyses of the solids obtained and NMR analyses are performed (see FIGS. 8 to 16).

Figure 8:
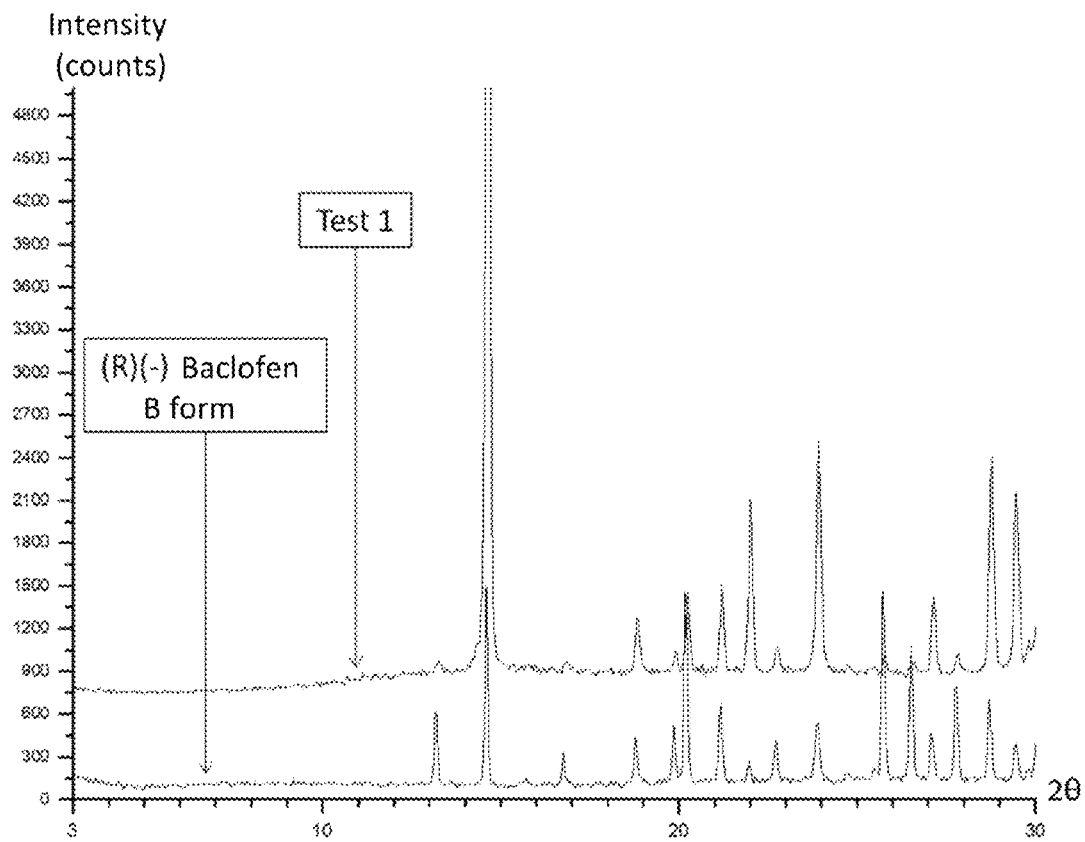
FIG. 8 is a comparison of the diffractograms, obtained by x-ray diffraction analysis, of the B form of (R)(-)-baclofen and of Test 1 of example 5.

Conclusion:

The x-ray diffraction analyses of the solids obtained demonstrate that all the solids obtained are constituted of enantiomerically pure baclofen in its B polymorphic form (see FIGS. 8, 10 and 12).

The NMR analyses confirm that the samples recovered are mainly constituted of baclofen with a few possible remaining traces of maleic acid (peak at 6 ppm) (see FIGS. 9, 11, 13, 14, 15 and 16).

The masses harvested and the purity indicate a good yield of the process (compared with the initial mass of baclofen dissolved). Tests 2 and 3 indicate that this yield can be optimized without affecting the purity.

The invention claimed is:

1. A racemic salt of baclofen hydrogen maleate (Bahma), wherein said racemic salt of baclofen hydrogen maleate has a melting/decomposition point of 164±1° C.

2. A process for resolving the (S) and (R) enantiomers of baclofen comprising the resolution of a baclofen hydrogen maleate salt as defined in claim 1.

3. The process as claimed in claim 2, wherein racemic baclofen is transformed into racemic baclofen hydrogen maleate salt in the presence of maleic acid, and in that said salt is then resolved by preferential crystallization to separate the two (S) and (R) enantiomers.

4. The process as claimed in claim 3, wherein the resolution of the racemic salt is performed by auto-seeded preferential crystallization or by seeded preferential crystallization.

5. The process as claimed in claim 4, wherein the resolution of the racemic salt is performed by auto-seeded preferential crystallization.

6. The process as claimed in claim 3, wherein the preferential crystallization is performed with a solvent selected from the group consisting of an alcoholic solvent, an aqueous solution, an acidic aqueous solution and mixtures thereof.

7. The process as claimed in claim 3, wherein the preferential crystallization is performed with an acidic aqueous solution, the acid being selected from the group consisting of hydrochloric acid, acetic acid and nitric acid.

8. The process as claimed in claim 7, wherein the preferential crystallization is performed with an aqueous hydrochloric acid solution.

9. The process as claimed in claim 7, wherein the preferential crystallization is performed with an aqueous 2 mol/L hydrochloric acid solution.

10. The process as claimed in claim 3, wherein the preferential crystallization is auto-seeded and in that it comprises the following steps:
    a) a volume V of a saturated solution of racemic Bahma salt in a solvent is prepared at a temperature $T_L$;
    b) at least 5% by weight of the first Bahma enantiomer to be recovered relative to the weight of the racemic Bahma salt is added;
    c) the mixture is heated to a temperature $T_B = T_L + 3°$ C.;
    d) a cooling programming law is applied to the mixture from $T_B$ to $T_F$, $T_F$ being below $T_B$, such that the mixture maintains a low supersaturation which favors the growth of the first Bahma enantiomer present in the form of crystals, while prohibiting the spontaneous nucleation of the second Bahma enantiomer dissolved in the solution;
    e) the crystals of the first Bahma enantiomer are harvested at the temperature $T_F$;
    f) substantially the same mass of racemic Bahma salt as the mass of the harvest made in the preceding step is added to the mixture, the difference is made up with solvent to reach the volume V and the new combined mixture is brought to the temperature $T_B$;
    g) the temperature $T_B$ is maintained for a time t so as to allow the system to return to thermodynamic equilibrium;
    h) the same cooling programming law as in step (d) is applied to the mixture prepared in step (g) containing the second Bahma enantiomer, so that the mixture maintains a low supersaturation during the crystallization so as to promote the growth of the second Bahma enantiomer present in the form of crystals while at the same time prohibiting the spontaneous nucleation of the first Bahma enantiomer present in the solution;
    i) the crystals of the second Bahma enantiomer are harvested at the temperature $T_F$;
    j) substantially the same mass of racemic Bahma salt as the mass of the harvest made in the preceding step is added to the mixture, the difference is made up with solvent to reach the volume V and the new combined mixture is brought to the temperature $T_B$;
    k) the temperature $T_B$ is maintained for a time t so as to allow the system to return to thermodynamic equilibrium;
    l) steps (d) to (k) are repeated to successively obtain one and then the other of the two enantiomers.

11. The process as claimed in claim 10, wherein the temperature $T_L$ ranges from 30 to 70° C.

12. The process as claimed in claim 11, wherein the temperature $T_L$ ranges from 40 to 60° C.

13. The process as claimed in claim 10, wherein the temperature $T_L$ is 50° C.

14. A process for the enantiomeric purification of baclofen hydrogen maleate (Bahma) salts, comprising the recrystallization of the Bahma salts in a solvent.

* * * * *